United States Patent [19]

Buchhold

[11] Patent Number: 5,460,186
[45] Date of Patent: Oct. 24, 1995

[54] APPARATUS FOR CONTROLLING PERIPHERAL DEVICES THROUGH TONGUE MOVEMENT, AND METHOD OF PROCESSING CONTROL SIGNALS

[76] Inventor: Niels Buchhold, Freiherr-vom-Stein Strasse 18, 61194 Niddatal 1, Germany

[21] Appl. No.: 228,745

[22] Filed: Apr. 18, 1994

[30] Foreign Application Priority Data

Apr. 20, 1993 [EP] European Pat. Off. ............. 93106409

[51] Int. Cl.⁶ ..................................................... A61B 5/10
[52] U.S. Cl. ...................................... 128/777; 340/825.19
[58] Field of Search .................................... 128/774, 772, 128/782; 340/825.19

[56] References Cited

U.S. PATENT DOCUMENTS

| | | | |
|---|---|---|---|
| 4,303,077 | 12/1981 | Lewin et al. ............................ | 128/777 |
| 4,383,535 | 5/1983 | Schorr .................................... | 128/777 |
| 4,728,812 | 3/1988 | Sheriff et al. .......................... | 128/777 |
| 4,765,345 | 8/1988 | Adib ....................................... | 128/777 |
| 4,783,656 | 11/1988 | Katz et al. .............................. | 128/777 |

*Primary Examiner*—Max Hindenberg
*Attorney, Agent, or Firm*—Henry M. Feiereisen

[57] ABSTRACT

Apparatus for controlling peripheral devices through tongue movement, includes a mouthpiece which is disposable in the oral cavity of a user and comprises a bar magnet which is connected to a tongue receptacle and securely supported by a multi-functional sealing ring of caoutchouc in a hollow cylindrical central housing. Accommodated in a sealed interior space of the housing are a plurality of Hall elements by which an analog Hall voltage commensurate with the motion of the bar magnet displaced by the tongue via the tongue receptacle is quantitatively and directionally detected.

12 Claims, 3 Drawing Sheets

APPARATUS FOR CONTROLLING PERIPHERAL DEVICES THROUGH TONGUE MOVEMENT, AND METHOD OF PROCESSING CONTROL SIGNALS

BACKGROUND OF THE INVENTION

The present invention refers to an apparatus for controlling peripheral devices through tongue movement, and to a method of processing or evaluating control signals for controlling peripheral devices through tongue movement.

It is generally known to assist disabled people, in particular quadriplegics with a control apparatus to operate peripheral devices such as computers, TV's, telephones and like devices by utilizing tongue movements. In this manner, handicapped people become capable to perform certain activities without assistance of others.

U.S. Pat. No. 4,728,812 discloses an oral machine controller for controlling operations of peripheral devices through tongue movement, and includes upper and lower dentition grips by which the upper and lower teeth in the jaw are locked in position. Through the tongue or tip of the tongue, a contact group or a potentiometer is actuated which is in communication with a processor, with the voltage potential being varied by linear movement of an actuator post along the length of the potentiometer. A drawback of this oral machine controller is its relatively large design which at operation is placed in front of the mouth. A further drawback is the required extreme shifting length to be covered by the actuator post in order to alter the voltage potential. For these reasons, this controller cannot be utilized to process rapidly following commands.

Swiss patent no. CH-PS 660,956 describes a control unit for handicapped persons by which a single contact carries out various control functions. Thus, commands must be sequentially processed via the single contact so that this control unit is also not suitable to process rapidly following instructions. Rather, the operator is required to proceed step-by-step to a desired menu in order to trigger the respective control function.

German patent publication DE-OS 1,943,824 discloses a control unit which is linked to a wheelchair and actuated by tongue movements to enable a quadriplegic to change the direction of motion. The tongue movement closes a respective current circuit between associated electrodes for motion of the wheelchair in a desired direction. Each direction of wheelchair motion is assigned a respective number of electrodes, resulting in an increased size of the overall control unit. Moreover, in order to actuate the electrode, the electrode plate must be moved to and from the operator, thus complicating the use of this control unit.

It is also known to place a tube in the mouth of a disabled person to transmit to a respective processor two instructions in form of aspirating or blowing through the pipe. Such aspiration and blowing technique has the same drawbacks with regard to a processing of rapidly incoming successive instructions as a processing of tongue-actuated electric contacts.

German patent no. DE 4,100,402 A1 discloses a mouth piece for disabled persons by which computers or other peripheral devices are controlled through use and processing of a tongue movement. The mouth piece resembles a joystick which is miniaturized so as to be usable during operation within the mouth of the operator. The mouth piece is actuated by the tongue which acts on a cage to close electrical contacts via a spring-loaded bar, with the closing of certain contacts in dependence on the tongue movement being quasi digital. Each case requires however a mechanical and electrical contact of the tongue-actuated pin with the pertaining contact leaves and center contact. During an extended use, the mouth piece is subjected to a corrosion of the contact surfaces so that a secure contacting cannot be ensured any more. Moreover, contact bounces may result in erroneous readings.

SUMMARY OF THE INVENTION

It is an object of the present invention to provide an improved apparatus for controlling peripheral devices through tongue movement obviating the afore-stated drawbacks.

In particular, it is an object of the present invention to provide an improved apparatus for controlling peripheral devices through tongue movement, which is disposed directly within the mouth or oral cavity and able to process rapidly incoming informations to generate respective electrical control signals for carrying out corresponding operations.

It is still another object of the present invention to provide an improved apparatus for controlling peripheral devices through tongue movement which is of such simple structure that operation of the apparatus can be intuitively and quickly learned.

It is yet another object of the present invention to provide an improved method of processing control signals for controlling peripheral devices through tongue movement.

These objects and others which will become apparent hereinafter are attained in accordance with the present invention by providing a mouth piece with a tongue receptacle which is connected via a bar magnet to a hollow cylindrical central housing defining an interior space which accommodates a plurality of Hall elements, with the tongue movement being transmitted via the bar magnet to the central housing and processed quantitatively and directionally by the Hall elements.

A control apparatus according to the present invention puts the operator not only in a position to use the apparatus for personal matters e.g. for switching on a TV or for actuating a telephone, but also creates new perspectives for the operator in the work environment by opening new professional activities to greatly enhance rehabilitation and quality of life.

The mouth piece remains operative and functional over an extended period and is easy to actuate. According to an essential feature of the present invention, the central housing is closed by a multi-functional sealing element in form of a caoutchouc ring that centers and securely supports the bar magnet which is connected to the tongue receptacle. In addition, the Hall elements are thus housed in a sealed environment in the interior space of the central housing to detect an analogous Hall voltage commensurate with the movement of the tongue-actuated bar magnet.

The provision of such a mouth piece permits not only an accurate detection of the actual displacement of the bar magnet but also an immediate and precise determination of the magnitude and direction of movement analogous with the tongue movement. Advantageously, the control apparatus lacks electromechanical contact elements and does also not require a provision of springs to support the bar magnet in a centered preset position so that the reliability of the entire control apparatus is significantly increased. Moreover, the control apparatus is comprised only of a minimal number of components so that the dimensions of the mouthpiece can be significantly reduced and is considerably more convenient for the operator to carry and to actuate.

The provision of a single multi-functional disk-shaped or plate-shaped sealing member of selected elasticity has also the advantage of protecting the mouth piece from saliva and of attaining a sensible actuating resistance while at the same time maintaining a set initial position of the bar magnet. The particular sealing member thus ensures a horizontal and vertical centering of the bar magnet.

Tests over an extended period have shown that already a slight touching of the tongue receptacle and a corresponding displacement of the bar magnet is sufficient to yield a defined output signal for further signal processing.

The particular design of the mouth piece and the manner of generating a signal as a function of a direction-dependent and path-dependent Hall voltage allows a processing of tongue-induced pulses which can be received in very rapid succession. This permits use of the control apparatus for a great variety of new applications including the motion of a vehicle, e.g. a wheelchair.

By instantly and rapidly converting the tongue movement i.e. the control commands and the quasi parallel signal processing, a vehicle is controllable in a very quick manner because a very short period elapses between the visual realization of e.g. an obstacle along the traveling path, the triggering of a command to bypass this obstacle and the issuance of a respective motion command to the steering unit.

Suitably, the control apparatus can be mounted to a wheelchair in such a manner that a quadriplegic can automatically pick up the mouth piece.

In addition to the operation of a wheelchair, the control apparatus according to the present invention can be modified through incorporation of a simple menu to actuate further peripheral devices via a transmitter which is mounted to the wheelchair and cooperates e.g. with a centrally arranged receiver. Suitably, the coded signal transmission between the transmitter on the wheelchair and the receiver is obtained via an infrared transmission path or through high frequency electromagnetic radiation.

It is also possible to equip the wheelchair with a special optoelectronic modem so that the operator is in a position to use—without any help from others—a public phone which has been equipped with a same modem for making telephone calls.

In accordance a method of the present invention, the signals of the Hall elements, which are arranged within the hollow cylindrical central housing of the mouth piece in a defined position, are processed in parallel transmission channels, with each Hall element being assigned within the transmission channel to an amplifier for boosting the output voltage. Since the Hall elements generate Hall voltages of unsteady pattern over the traveled path by the bar magnet relative to the Hall elements, these Hall voltages cannot be directly utilized for an analogous control of the wheelchair. Therefore, the amplified voltage signal of each channel is subjected to an analog/digital conversion and to a linearization through characteristic approximation by means of a microcontroller. The linearized signals are then fed into a data transfer unit for control of a conventional PC or transmitted to a digital/analog converter for immediate analogous control of e.g. servo motors of a steering unit to control the wheelchair.

BRIEF DESCRIPTION OF THE DRAWING

The above and other objects, features and advantages of the present invention will now be described in more detail with reference to the accompanying drawing in which.

DETAILED DESCRIPTION OF PREFERRED EMBODIMENTS

Figure 1:
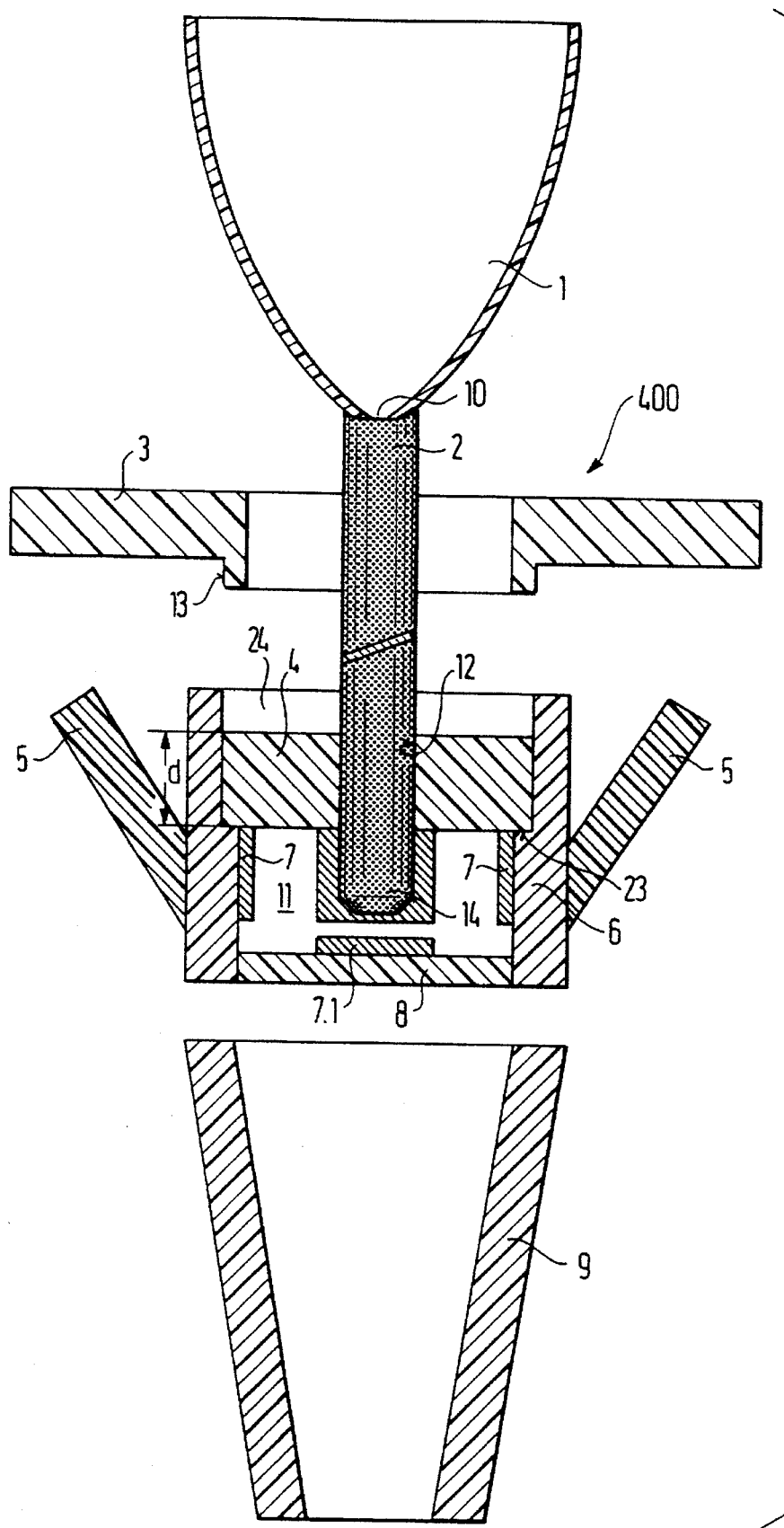
FIG. 1 is a partly exploded schematic longitudinal section of one embodiment of an apparatus for controlling peripheral devices through tongue movement, in accordance with the present invention.

Throughout all the Figures, the same or corresponding elements are always indicated by the same reference numerals.

Referring now to the drawing, and in particular to FIG. 1, there is shown a schematic longitudinal section of an apparatus for controlling peripheral devices through tongue movement. The control apparatus is provided in form of a mouth piece 400 (FIG. 2) which includes a tongue receptacle 1 of essentially funnel-shaped configuration. The tongue receptacle 1 is provided in the tapered lower end with a central bore 10 for receiving one end of a bar magnet 2. The bar magnet 2 may be of cylindrical or any other suitable cross section and extends through a central bore 12 of a sealing member 4 which is of elastic material such as caoutchouc and configured in form of a ring or a disk.

The sealing member 4 is fitted securely in an inner shoulder 23 of a hollow cylindrical central housing 6 to seal the central housing 6 to the outside. The lower end of the central housing 6 is closed by a bottom plate 8 which may be glued thereto. The central housing 6 thus defines together with the opposing sealing member 4 and the bottom plate 8 an interior space 11 which accommodates a plurality of sensors, preferably in form of Hall probes or elements 7. The Hall elements 7 are arranged about the inside wall of the central housing 6 in opposite relationship e.g. in north/south direction, east/west direction, with a further Hall element 7.1 being mounted centrally on the inside wall of the bottom plate 8 opposite to the lower end of the bar magnet 2.

It will be understood by persons skilled in the art that the Hall elements may be substituted by similar contactless-operated sensors.

As shown in FIG. 1, the sealing member 4 is provided with a thickness d which is selected in dependence of the elastic properties of the material in order to securely guide the bar magnet 2 in response to a movement of the tongue receptacle 1 and to ensure a sufficient sealing of the space 11. By suitably selecting the elastic properties of the sealing member 4 and the ratio between the diameter of the bar magnet 2 and the inner bore 12 of the sealing member 4 as well as the thickness d and the inner diameter of the cylindrical central housing 6, the movement of the bar magnet 2 is countered by a tangible but yet sufficiently low resistance so that a sensitive and rapid actuation of the tongue receptacle 1 through the tongue of the operator is possible.

Although not shown in the drawing, the bottom plate 8 is provided with openings for receiving the connecting cables 18D (FIG. 2) for the Hall elements 7, 7.1. These openings are suitably sealed by an epoxy resin or a polymer material.

As further shown in FIG. 1, the sealing member 4 does not reach the top edge of the central housing 6 so that the central housing 6 includes an upper open space 24 for receiving a top plate 3 to close the central housing 6. The top plate 3 is provided with an integral step-shaped projection 13 which protrudes downwards from the top plate 3 into the upper space 24. Suitably, the top plate 3 is glued to the central housing 6 and has an outer diameter which is significantly greater than the diameter of the hollow cylindrical central housing 6.

A caoutchouc ring 5 is further attached at an angle to the outside wall of the central housing 6 to facilitate support and actuation of the mouth piece 400 within the oral cavity of the operator.

Mounted to the bottom plate 8 is a lower housing pad 9 for receiving and guiding the connecting cables 18D to the Hall elements 7, 7.1. The housing part 9 is advantageously of conical configuration and is butt-joint to the central housing 6 through gluing.

The following nonlimiting examples of dimensions for individual components best illustrates the miniaturized design of the mouthpiece. For example, the central housing 6 has an outer diameter of about 10 mm at a height of 7 mm. The thickness of the sealing member 4 may be e.g. about 3 mm and the diameter of the bar magnet 2 may be about 2 mm.

It is in particular advantageous to make a sealing member 4 of natural caoutchouc material with the following dimensional relationships:

Ratio of the diameter of the central bore 12 to the thickness d of the sealing member 4 and the diameter of the sealing member 4 of 1:1-1.5:3-4.

In order to further improve the accuracy of processing the movement of the tongue receptacle 1 and the bar magnet 2 mounted thereto, in particular with regard to the central Hall element 7.1, the bar magnet 2 has a beveled end 14 which projects into the space 11 of the central housing 6.

The Hall elements 7, 7.1 are controlled and operated in such a manner that an offset voltage is set for the initial state of the bar magnet 2 which is commensurate with the central position thereof. The Hall voltage of the surrounding Hall elements 7, 7.1 varies in dependence on the movement, intensity and direction of displacement of the bar magnet 2. By evaluating and comparing the varying voltages, optionally in relationship with a time period, it is possible to securely detect also small rapidly occurring successive shifts of the bar magnets 2.

The mouth piece 400 according to the present invention is capable to securely detect also quasi superimposed motions e.g. a lateral movement with an axial movement and to transmit clearly defined instructions.

Figure 2:
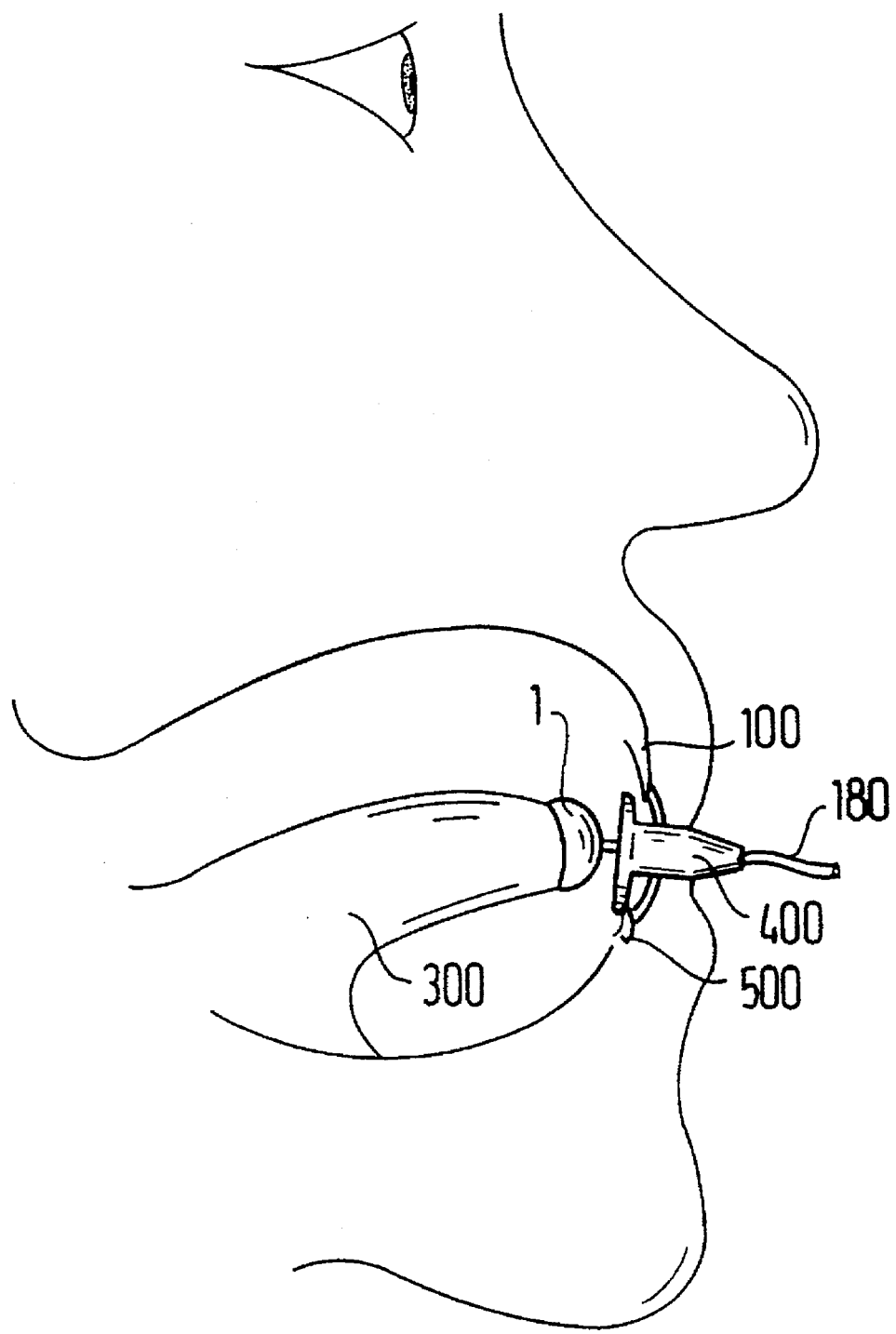
FIG. 2 is a principal illustration of attachment of the control apparatus of FIG. 1 in the mouth of a quadriplegic.

Turning now to FIG. 2, there is shown a principal illustration of placement of the control apparatus or mouth piece 400 in the mouth of the operator, with the mouth piece 400 being clamped and fixed between the upper teeth 100 and lower teeth 500. The tongue 300 is intimately received within the funnel-shaped tongue receptacle 1 so that any movement of the tongue 300 is transmitted via the tongue receptacle 1 to the bar magnet 2 (FIG. 1) and detected by the Hall elements 7, 7.1 (FIG. 1 ).

The small dimensions of the mouth piece 400 and the provision of flexible connections in form of only a few electric cables 18D for connection to the processor or evaluator unit essentially allows an unobstructed movement of the head of the operator.

As shown in FIG. 2, the mouth piece 400 is essentially disposed within the oral cavity so as to quickly trigger distinct signals commensurate with the movement of the tongue 300. When attaching the mouth piece 400 to an exemplified telescopic bar or a movable swan-neck arm e.g. of the wheelchair, the disabled person can easily and repeatedly pick up and release the mouth piece 400.

All essential elements of the mouth piece 400 are made e.g. of a compatible plastic material such as a cold polymerizate available under the trade name Paladur.

Figure 3:
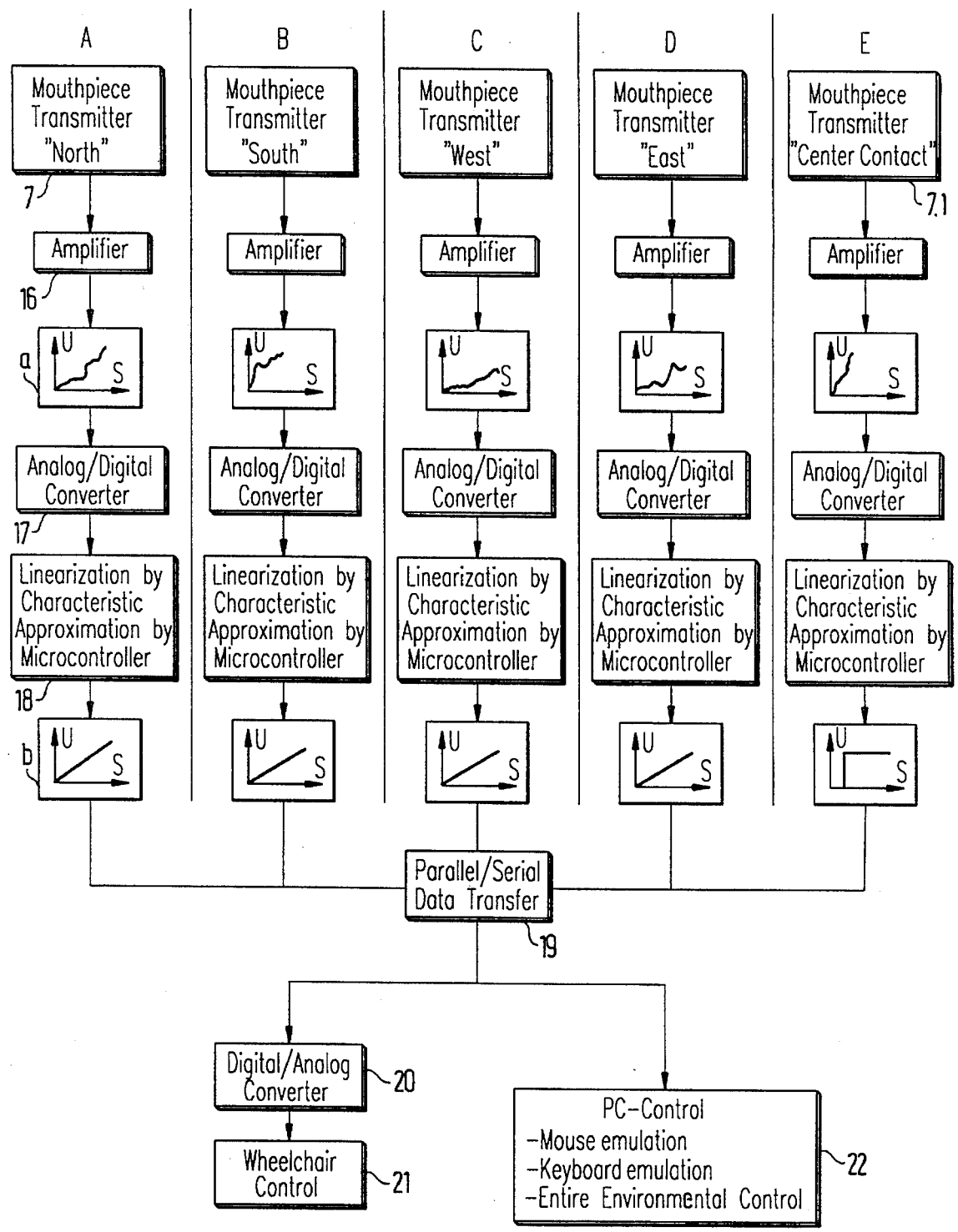
FIG. 3 is a block diagram illustrating a signal processing method according to the present invention.

Referring now to FIG. 3, there is shown a schematic block diagram illustrating the steps for processing signals in accordance with the present invention. The nonlimiting example of FIG. 3 illustrates a five-channel arrangement, with each Hall element being located at a defined location in the central housing 6 of the mouth piece 400 and assigned to a channel A-E for detecting a movement of the bar magnet 2 in direction "north", "south", "west", "east" and "central". Depending on the movement of the tongue-actuated bar magnet 2, the Hall elements 7, 7.1 generate corresponding output signals which are boosted by successive arranged amplifiers 16 and transmitted to an analog/digital converter 17. Since the pattern of the output signals (voltages U) generated by the Hall elements 7, 7.1 is unsteady as plotted against the path S, as symbolically shown by the graphical illustrations a), an immediate processing of these output signals is not or only insufficiently feasible. Therefore, the amplified output signal in each channel A-E is digitized by a subsequent analog/digital conveder 17 and then linearized through characteristic approximation by means of a microcomputer 18. Graphical illustrations b), show the linearized output signals. The thus linearized output signals are transmitted to a parallel/serial data transfer unit 19 which yields an output signal which can be transmitted either to a digital/analog converter 20 for conversion to an analogous signal which e.g. can be used directly for analogous control of the wheelchair, or directly to a PC control unit 20 for operating peripheral devices 22, such as e.g. mouse emulation, keyboard simulation or overall environmental control.

The control apparatus or mouth piece 400 of the present invention, which is easy to handle and quasi intuitively learnable, improves the quality of life for a disabled person and creates a real rehabilitation by utilizing all existing capabilities of the operator. The possibility of processing rapidly following instructions in correspondence with the tongue movement, enables the operator to carry out not only simple switching processes but also complicated control tasks such as actuating a CAD work station. The use of the control apparatus according to the invention thus enables a handicapped person to creatively work with a computer.

While the invention has been illustrated and described as embodied in an apparatus for controlling peripheral devices through tongue movement, and method for processing control signals, it is not intended to be limited to the details shown since various modifications and structural changes may be made without departing in any way from the spirit of the present invention.

What is claimed as new and desired to be protected by Letters Patent is set forth in the appended claims:

I claim:

1. Apparatus for controlling peripheral devices through tongue movement, comprising a mouthpiece disposable in the oral cavity of a user and including a tongue receptacle for attachment to the tongue;

a hollow cylindrical central housing operatively connected to said receptacle and having a closed bottom, said central housing defining an interior space accommodating a plurality of Hall elements;

an elastic sealing member fitted in an upper portion of said central housing; and a bar magnet extending from said receptacle into said interior space of said central housing and being securely guided and centered in a bore of said sealing member, said bar magnet transmitting a tongue movement from said receptacle to said central housing, with the tongue movement being detected quantitatively and directionally by the Hall elements.

2. Apparatus as defined in claim 1, wherein said central housing includes a bottom plate for closing the bottom, said Hall elements being arranged about the inner circumference of said central housing in opposite relationship, with at least one Hall element being provided at a central location on the inside of said bottom plate.

3. Apparatus as defined in claim 1 wherein said bar magnet has one beveled end which projects into said interior space of said central housing.

4. Apparatus as defined in claim 1 wherein said elastic sealing member is of disk-like configuration with a width and a diameter, said bore of said sealing member being defined by a diameter having a ratio to said width and to said diameter of said sealing member of 1:1-1.5:3–4.

5. Apparatus as defined in claim 1 wherein central housing has an open top closable by a top pate which extends over and beyond said central housing, said top plate having a stepped projection received in said central housing.

6. Apparatus as defined in claim 1, and further comprising a caoutchouc ring extending at an angle from the outer circumference of said central housing.

7. Apparatus for controlling peripheral devices through tongue movement, comprising:

a tongue receptacle for attachment to the tongue;

a central housing defining an interior space an elastic sealing member fitted in an upper portion of said central housing;

sensor means accommodated in said interior space of said central housing;

a bar magnet extending from said receptacle into said interior space of said central housing, said bar magnet being securely guided and centered by said sealing member and cooperating with said sensor means in such a manner that a tongue movement is transmitted to said bar magnet and detected by said sensor means for generating an output signal commensurate with the tongue movement; and processing means receiving said output signals for controlling a peripheral device.

8. Apparatus as defined in claim 7 wherein said processing means includes an amplifier operatively connected to said sensor means for boosting the output signal, an analog/digital converter arranged in succession of said amplifier for digitizing the boosted output signal, and a microcomputer for linearization of the digitized output signal.

9. A method of processing control signals for controlling peripheral devices through tongue movement, comprising the steps of:

attaching a mouthpiece to the tongue, with the mouth piece accommodating Hall elements for detecting a tongue movement via a bar magnet by providing a voltage signal commensurate with the tongue movement;

assigning each Hall element to a signal processing channel;

digitizing the voltage signal in each signal processing channel; and linearizing the digitized voltage signal through characteristic approximation to generate a linearized output signal.

10. A method as defined in claim 9, and further comprising the step of converting the linearized output signal into an analog signal for controlling a peripheral device.

11. A method as defined in claim 9 wherein said linearizing step is carried out by means of a microcomputer.

12. A method as defined in claim 9, and further comprising the step of combining the output signals of the signal processing channels in a parallel/serial data transfer unit for selectively supplying a PC-control for influencing peripheral devices and a digital/analog converter for generating analog control signals.

* * * * *

UNITED STATES PATENT AND TRADEMARK OFFICE
CERTIFICATE OF CORRECTION

PATENT NO. : 5,460,186
DATED : Oct. 24, 1995
INVENTOR(S) : Niels Buchhold

It is certified that error appears in the above-indentified patent and that said Letters Patent is hereby corrected as shown below:

Column 4, line 67 and Column 5, line 66, change "18D" to --180--;

Column 6, line 30, change "conveder" to --converter--;

Column 5, line 17, change "18D" to --180--

Signed and Sealed this

Twenty-seventh Day of February, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,460,186
DATED : October 24, 1995
INVENTOR(S) : Niels Buchhold

It is certified that error appears in the above-identified patent and that said Letters Patent is hereby corrected as shown below:

Column 6, line 40, change "simulation" to --emulation--.

Signed and Sealed this

Thirtieth Day of April, 1996

Attest:

Attesting Officer

BRUCE LEHMAN

Commissioner of Patents and Trademarks